(12) United States Patent
Kim et al.

(10) Patent No.: US 12,257,070 B2
(45) Date of Patent: Mar. 25, 2025

(54) PAIN ASSESSMENT METHOD BASED ON DEEP LEARNING MODEL AND ANALYSIS DEVICE

(71) Applicant: NEUROGRIN INC., Seoul (KR)

(72) Inventors: Sun Kwang Kim, Seoul (KR); Myeong Seong Bak, Seoul (KR); Hee Ra Yoon, Seoul (KR); Sang Jeong Kim, Seoul (KR); Geehoon Chung, Seoul (KR)

(73) Assignee: NEUROGRIN INC., Seoul (KR)

( * ) Notice: Subject to any disclaimer, the term of this patent is extended or adjusted under 35 U.S.C. 154(b) by 414 days.

(21) Appl. No.: 17/846,772

(22) Filed: Jun. 22, 2022

(65) Prior Publication Data
US 2022/0323003 A1    Oct. 13, 2022

Related U.S. Application Data

(63) Continuation of application No. PCT/KR2020/006221, filed on May 12, 2020.

(30) Foreign Application Priority Data

Dec. 23, 2019  (KR) .................. 10-2019-0173382
May 7, 2020   (KR) .................. 10-2020-0054412

(51) Int. Cl.
*A61B 5/00*     (2006.01)
*G06T 7/11*     (2017.01)
*G06V 40/16*    (2022.01)

(52) U.S. Cl.
CPC .......... *A61B 5/4824* (2013.01); *A61B 5/7264* (2013.01); *G06T 7/11* (2017.01); *G06V 40/168* (2022.01)

(58) Field of Classification Search
CPC . A61B 5/4824; A61B 5/7264; G06F 2218/22; G06V 40/168;
(Continued)

(56) References Cited

U.S. PATENT DOCUMENTS 11,779,269 B2* 10/2023 Nakae .................. A61B 5/4824
                                                    600/544
2016/0302720 A1* 10/2016 John ...................... A61B 5/369
(Continued)

FOREIGN PATENT DOCUMENTS

CA        2403974 A1 * 10/2001
JP     2010523226 A  *  4/2008
(Continued)

OTHER PUBLICATIONS

Alex Novaes Santana et al.,"Using Deep Learning and Resting-State fMRI to Classify Chronic Pain Conditions," Dec. 17, 2019, Frontiers in Neuroscience,vol. 13,Article 1313,Dec. 2019,pp. 1-9.*
(Continued)

*Primary Examiner* — Omar S Ismail
(74) *Attorney, Agent, or Firm* — Paratus Law Group, PLLC

(57) ABSTRACT

Disclosed is a pain assessment method using a deep learning model, the pain assessment method including operations of receiving, by an analysis device, an image indicating activity in a specific brain area of a subject animal and allowing the analysis device to input images of regions of interest in the image into a neural network model and assess the pain of the subject animal according to a result output by the neural network model.

13 Claims, 16 Drawing Sheets

(58) Field of Classification Search
CPC . G06T 2207/10056; G06T 2207/20081; G06T 2207/20084; G06T 2207/20104; G06T 2207/30016; G06T 7/0016; G06T 7/11; G16H 50/20

See application file for complete search history.

(56) References Cited

U.S. PATENT DOCUMENTS

| | | | | |
|---|---|---|---|---|
| 2018/0228423 | A1* | 8/2018 | Intrator | A61B 5/726 |
| 2018/0263585 | A1* | 9/2018 | Weiss | A61B 6/50 |
| 2019/0320974 | A1* | 10/2019 | Alzamzmi | A61B 5/746 |
| 2020/0057937 | A1* | 2/2020 | Ushakov | G06N 3/063 |

FOREIGN PATENT DOCUMENTS

| | | | |
|---|---|---|---|
| KR | 10-2019-0073330 | A | 6/2019 |
| KR | 10-2019-0100888 | A | 8/2019 |
| KR | 10-2027368 | B1 | 10/2019 |
| KR | 10-2031983 | B1 | 10/2019 |

OTHER PUBLICATIONS

Xiao-Su Hu et al.,"Feasibility of a Real-Time Clinical Augmented Reality and Artificial Intelligence Framework for Pain Detection and Localization From the Brain," Jun. 28, 2019, Journal of Medical Internet Research 2019,vol. 21, issue 6, pp. 1-8.*

Ishmail Abdus-Saboor et al., "Development of a Mouse Pain Scale Using Subsecond Behavioral Mapping and Statistical Modeling," 6ht Aug. 2019, Cell Reports 28,pp. 1622-1631.*

Joseph J. Titano et al.,"Automated deep-neural-network surveillance of cranial images for acute neurologic events," Aug. 13, 2018,Nature Medicine,vol. 24,Sep. 2018,pp. 1337-1340.*

P.Y. Geha et al.,"Brain activity for spontaneous pain of postherpetic neuralgia and its modulation by lidocaine patch therapy," Oct. 25, 2006, Pain 128 (2007),vol. 128, Issues 1-2,pp. 92-96.*

Debbie L Morton et al.,"Brain imaging of pain: state of the art," Sep. 8, 2016,Journal of Pain Research,pp. 613-620.*

Yiheng Tu et al.,"Decoding Subjective Intensity of Nociceptive Pain from Pre-stimulus and Post-stimulus Brain Activities," Apr. 14, 2016, Frontiers in Computational Neuroscience, Apr. 2016, vol. 10, Article 32, pp. 1-9.*

Janete Shatkoski Bandeira et al.,"Functional Spectroscopy Mapping of Pain Processing Cortical Areas During Non-painful Peripheral Electrical Stimulation of the Accessory Spinal Nerve," Jun. 13, 2019, Frontiers in Human Neuroscience, Jun. 2019, vol. 13, Article 200, pp. 1-11.*

Mohammad Hasan et al.,"Somatosensory Change and Pain Relief Induced by Repetitive Transcranial Magnetic Stimulation in Patients With Central Poststroke Pain," Jun. 17, 2014,Neuromodulation: Technology at the Neural Interface,vol. 17, Issue 8, Dec. 2014,pp. 731-733.*

Justin E. Brown et al.,"Towards a Physiology-Based Measure of Pain: Patterns of Human Brain Activity Distinguish Painful from Non-Painful Thermal Stimulation," Sep. 13, 2011, PLoS ONE,Sep. 2011,vol. 6,Issue 9,pp. 1-6.*

Maria Joao Rosa et al.,"Decoding the matrix: Benefits and limitations of applying machine learning algorithms to pain neuroimaging," May 2014, Pain 155 (2014),pp. 864-866.*

International Search Report for PCT/KR2020/006221 mailed Sep. 16, 2020 from Korean Intellectual Property Office.

Korean Office Action for related KR Application No. 10-2020-0054412 mailed May 31, 2021 from Korean Intellectual Property Office.

* cited by examiner (A)

(B)

(A)

(B)

(C)

(D)

(A)

(B)

(A)

(B)

(A)

(B)

(A)

(B)

(A)

(B)

(A)

(B)

(A)

(B)

(C)

PAIN ASSESSMENT METHOD BASED ON DEEP LEARNING MODEL AND ANALYSIS DEVICE

CROSS-REFERENCE TO PRIOR APPLICATIONS

This application is a Continuation Application of PCT International Patent Application No. PCT/KR2020/006221 (filed on May 12, 2020), which claims priority to Korean Patent Application Nos. 10-2019-0173382 (filed on Dec. 23, 2019) and 10-2020-0054412 (filed on May 7, 2020), which are all hereby incorporated by reference in their entirety.

BACKGROUND

The following technique relates to a pain evaluation technique using an animal model.

Animal pain models are essential for understanding the mechanism of pain and developing effective therapeutic drugs or treatments. An effort to detect a human-like spontaneous pain in animal model is ongoing. Conventional spontaneous pain assessment methods were mainly based on facial expression changes according to pain or a behavioral experiment utilizing the compensation action of pain.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a pain assessment method using a deep learning model includes operations of receiving, by an analysis device, an image indicating activity in a specific brain area of a subject animal and allowing the analysis device to input images of regions of interest in the image into a neural network model and assess the pain of the subject animal according to a result output by the neural network model. Each region of interest is a region indicating the activity of an individual cell, and the analysis device inputs information generated based on the images of the regions of interest into a plurality of input layers of the neural network model.

In another aspect, there is provided a pain analysis device using a deep learning model includes an input device configured to receive an image indicating activity in a specific brain area of a subject animal, a storage device configured to store a bidirectional recurrent neural network model that receives an image for brain activity and assesses a pain state, and a computing device configured to input images of regions of interest in the image into a plurality of input layers of the bidirectional recurrent neural network model and assess the pain of the subject animal according to a result output by the bidirectional recurrent neural network model.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
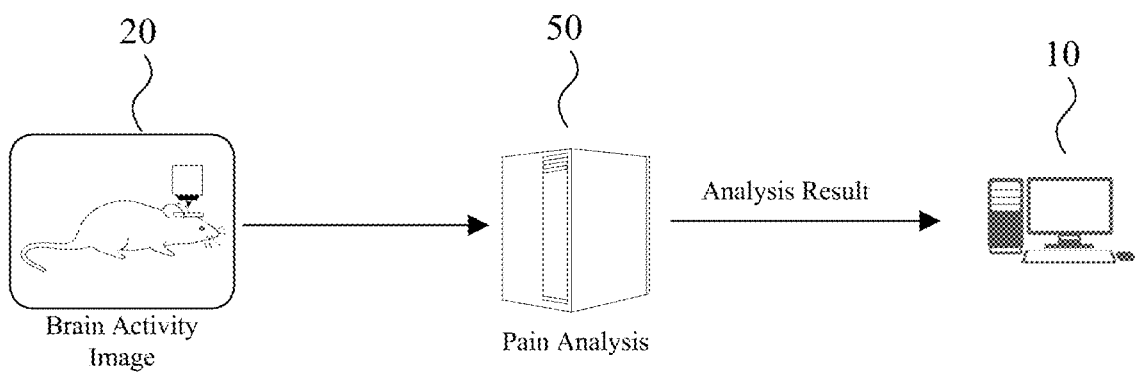
FIG. 1 is an example of a pain assessment system using an animal model.
Figure 1:
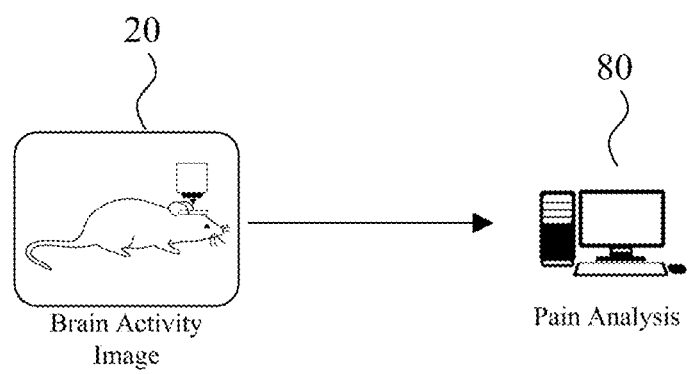

As the following description may be variously modified and have several example embodiments, specific embodiments will be shown in the accompanying drawings and described in detail below. It should be understood, however, that there is no intent to limit the following description to the particular forms disclosed, but on the contrary, the following description is to cover all modifications, equivalents, and alternatives falling within the spirit and scope of the invention.

In addition, the terms such as "first," "second," "A," and "B" may be used to describe various elements, but these elements are not limited by these terms. These terms are used to only distinguish one element from another element. For example, a first element may be called a second element, and a second element may also be called a first element without departing from the scope of the following description. The term "and/or" means any one or a combination of a plurality of related items.

It should be understood that singular forms are intended to include plural forms unless the context clearly indicates otherwise, and it should be further understood that the term "comprise," "include," or "have" as used herein specify the presence of stated features, numbers, steps, operations, elements, components, or a combination thereof, but do not preclude the presence or addition of one or more other features, numbers, steps, operations, elements, components, or combinations thereof.

Prior to a detailed description of the drawings, it should be clarified that division of components in the present specification is performed merely based on main functions performed by the respective components. That is, two or more components which will be described later may be integrated into a single component or, alternatively, a single component may be divided into two or more components depending on subdivided functions. Further, it is apparent that each of the components, which will be described later, may additionally perform some or all of functions performed by other components in addition to main functions performed thereby, and some of the main functions performed by the respective components may be shared with other components and may be performed.

In addition, the respective steps of the above method may be performed in a sequence different from a described sequence unless the context clearly defines a specific sequence. That is, the respective steps may be performed in the same order as described, substantially simultaneously, or in reverse order.

In the following description, pain is assessed based on information on brain activity of a test subject. Basically, the following technique may be applied to a pain assessment technique using an animal model. An animal used as an animal model is typically a mouse. However, various different animals may be used as an animal for pain assessment. Hereinafter, animals used for pain assessment are referred to as subject animals.

In the following description, an image showing brain activity of a subject animal is used. Hereinafter, an image showing brain activity is referred to as a brain activity image. A brain activity image may be acquired through various image techniques or apparatuses.

A brain activity image may be an image for a specific area of a brain. In this case, the specific area of the brain corresponds to an area showing the activity of the brain for pain detection. (1) The specific area of the brain may be at least one of a plurality of areas of the brain. For example, the plurality of areas may include a cerebral cortex, a cerebellum, a brain stem, and the like. (2) Furthermore, the plurality of areas may be some areas associated with specific functions. For example, the specific area of the brain may be the primary somatosensory area (S1) of the cerebral cortex.

A brain activity image may be acquired by various techniques. For example, a brain activity image may be acquired by any one of various techniques, such as single-photon imaging, two-photon imaging, and multi-photon imaging. For example, two-photon imaging may express the degree of brain activity by the fluorescence brightness change rate(delta F).

The brain activity image shows the activity of specific cells distributed in a corresponding area. (1) The brain activity image may show the activity of cortical nerve cells. For example, the brain activity image may be an image that shows the activity of nerve cells in the primary somatosensory area of the cerebral cortex. Basically, the brain activity image shows the activity of a plurality of nerve cells. (2) Furthermore, the brain activity image may be an image showing the activity of cerebellar Bergmann glial cells. Bergmann glial cells correspond to glial cells, not nerve cells. Even in this case, the brain activity image shows the activity of a plurality of Bergmann glial cells. Accordingly, the brain activity image includes information indicating the degree of activity of a plurality of cells in at least one of various regions of the brain.

In the following description, brain activity images acquired by various experimental approaches are used. In the following description, there is no reason why subjects for pain assessment are necessarily limited to animals. That is, the following description may be utilized as a pain evaluation technique for various subjects (including humans) capable of having their brain activity images acquired.

In the following description, a machine learning model for analyzing a brain activity image is used. Machine learning is a field of artificial intelligence and refers to the field of developing algorithms for computer learning. A machine learning model or a learning model refers to a model developed for computer learning. The learning model includes various models such as artificial neural networks and decision trees depending on the approach.

Various models such as Recurrent Neural Network (RNN), Feedforward Neural Network (FFNN), and Convolutional Neural Network (CNN) have been studied for neural network models. An analysis technique to be described below may use RNN to use time-series images acquired for a certain period of time. It will be appreciated that a neural network model for pain assessment is not necessarily implemented only using RNN. Hereinafter, for convenience of description, the following description will focus on the RNN model.

FIG. 1 is an example of a pain assessment system using an animal model. FIG. 1 shows two types of systems. Analysis devices 50 and 80 analyze an image acquired through an animal model to assess the pain of the animal model. In FIG. 1, each analysis device is shown in the form of a network server 50 or a computer terminal 80.

FIG. 1A is an example of a system including the analysis server 50.

An image generating apparatus 20 generates a brain activity image of an animal that is a test subject. Hereinafter, it is assumed that the image generating apparatus generates a brain activity image using a two-photon microscope. A two-photon microscope may generate images for analyzing the activity of the brain of a subject animal. It is assumed that the image generating apparatus measures an activation signal of a specific brain area of the subject animal. The subject animal may be in a state in which specific pain is induced or a state in which a pain relief drug is administered.

The image generating apparatus 20 generates brain activity images of the subject animal for a certain period of time. That is, the image generating apparatus 20 generates time-series data, which indicates images in a certain interval.

The analysis server 50 receives a brain activity image generated by the image generating apparatus 20. The analysis server 50 analyzes the brain activity image and assesses the pain of the subject animal. The analysis server 50 may routinely pre-process the brain activity image. The analysis server 50 may assess pain by inputting the preprocessed data into the learning model. The learning model may be a model for processing the time-series data. The learning model is a pre-trained model. The analysis server 50 may deliver the analysis result to a user terminal 10.

FIG. 1B is an example of the analysis device in the form of a computer terminal 80.

An image generating apparatus 20 generates a brain activity image of an animal that is a test subject. The image generating apparatus 20 may generate a two-photon image for a specific area of a brain. The subject animal may be in a state in which specific pain is induced or a state in which a pain relief drug is administered. The image generating apparatus 20 generates brain activity images of the subject animal for a certain period of time. That is, the image generating apparatus 20 generates time-series data, which indicates images in a certain interval.

The computer terminal 80 receives a brain activity image generated by the image generating apparatus 20. The computer terminal 80 analyzes the brain activity image and assesses the pain of the subject animal. The computer terminal 80 may routinely pre-process the brain activity image. The computer terminal 80 may analyze the brain activity image using a program including a learning model. The computer terminal 80 may assess pain by inputting the preprocessed data into the learning model. The learning model is a pre-trained model. The computer terminal 80 may output the analyzed result.

Figure 2:
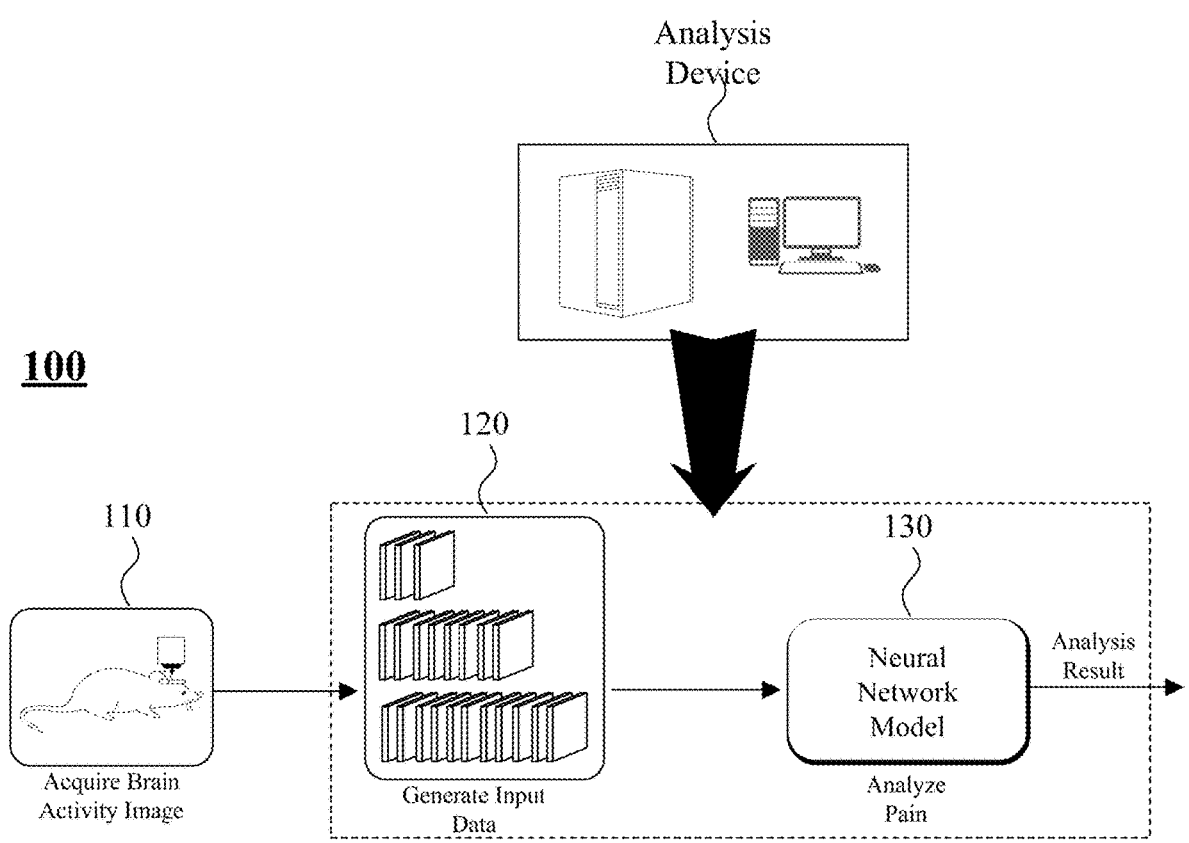
FIG. 2 is an example of a pain assessment process using a deep learning model.

FIG. 2 is an example of a pain assessment process 100 using a deep learning model. First, a brain activity image for a subject animal is acquired (110). The brain activity image of the subject animal is generated using an image generating apparatus such as a two-photon microscope.

The analysis device receives the brain activity image. The analysis device may be a device such as the above-described analysis server 50 or computer terminal 80. Furthermore, the analysis device may be implemented in various forms. For example, the analysis device may be implemented in the form of a portable device such as a smartphone carried by the researcher.

The analysis device may routinely pre-process the brain activity image (120). For example, the analysis device may uniformly divide time-series data. The pre-processing process will be described below. This process corresponds to a process of generating input data to be input into a neural network model.

The analysis device has a pre-trained neural network model. The neural network model will be described in detail below. The analysis device inputs the brain activity image or the preprocessed image into the neural network model (130). The analysis device may assess the pain of the subject animal using information output by the neural network model.

Figure 3:
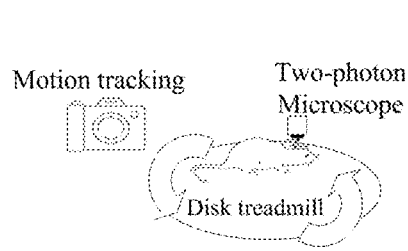
FIG. 3 is an example of a two-photon microscopy image showing brain activity.
Figure 3:
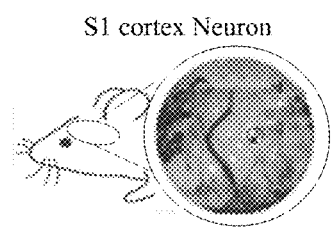
Figure 3:
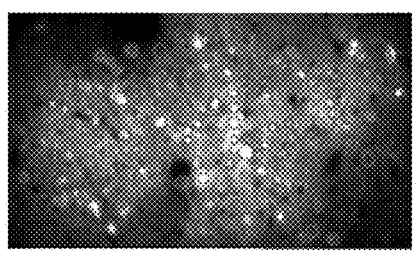
Figure 3:
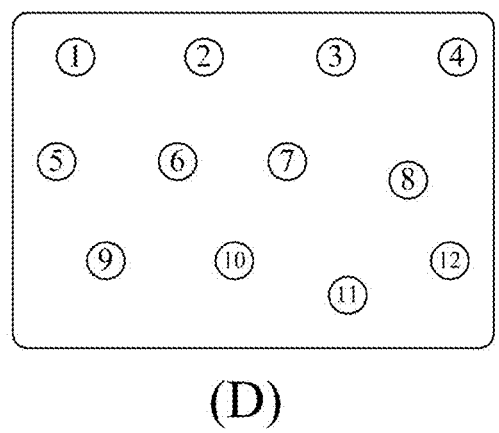

FIG. 3 is an example of a two-photon microscopy image showing brain activity. FIGS. 3A to 3C are examples of a process of acquiring an activity image of a nerve cell of an area S1 of the cerebral cortex. The subject animal is a mouse.

FIG. 3A is an example in which an image of the activity of an S1 neuron while a two-photon fluorescence microscope is fixed on the head.

The brain activity may be measured based on a calcium ($Ca^{2+}$) signal. A genetically encoded calcium indicator (GECI), which is a fluorescent label responsive to calcium concentration, may be used. The GECI is useful for imaging activity at the cellular level.

There are various methods for calcium imaging. The following description is not limited to specific calcium imaging techniques. For calcium imaging, it may be necessary to inject GCaMP6 into the subject animal.

Typically, a two-photon microscope measures an optical signal by selectively exciting a fluorescent molecule with a laser beam, similar to a confocal microscope. In general, the two-photon microscope should be fixed on the head of the subject animal. Accordingly, in order to image a freely moving subject animal, a treadmill may be installed on the bottom of the two-photon microscope to acquire an image for the moving subject animal. In this case, motion tracking may be performed simultaneously with calcium imaging by photographing the movement of the subject animal with a separate external camera.

Compared to a single-photon microscope, a two-photon microscope may allow observation of cells at a deeper level using light of a longer wavelength. Furthermore, it is also possible to use a multi-photon microscope such as a three-photon microscope.

Meanwhile, it is also possible to observe a neural activity signal of the subject animal using a single-photon microscope. The single-photon microscope is made small and light and may be attached to the head of the subject animal and then used.

FIG. 3B is a schematic diagram of the S1 area of a mouse where in vivo calcium imaging is performed and an example of the appearance of the cerebral cortex seen through an imaging window.

FIG. 3C is an example of an area showing brain activity in the cerebral cortex. FIG. 3C shows a fluorescent signal observed through a two-photon fluorescence microscope in a corresponding area. In this case, a brain activity image shows the activity of a plurality of nerve cells. The analysis device may assess pain on the basis of the brain activity image as shown in FIG. 3C.

The analysis device may set a region of interest without using the entire brain activity image and may assess pain based on the region of interest. As described above, the brain activity image shows the activity of the plurality of cells. Accordingly, the regions of interest in the brain activity image may be areas where the plurality of cells are located. The regions of interest may be specific cells among the plurality of cells. In FIG. 3C, an area marked with a red circle is a region of interest.

FIG. 3D is a schematic diagram of a region of interest set in a brain activity image. In FIG. 3D, areas marked with a circle are examples of the region of interest. The regions of interest were identified with different indices. As will be described later, activity data of a nerve cell in a region of interest with a specific index may be input into a specific input layer of a neural network.

The analysis device may extract a region of interest from the brain activity image. The analysis device may determine an area having a fluorescence brightness change rates greater than or equal to a predetermined value as a region of interest by using an image processing program and may identify the corresponding area. Alternatively, the analysis device may detect a region of interest using a separate neural network for detecting regions of interest. In this case, the analysis device may use various learning models used to detect a specific area or object in an image. For example, the analysis device may detect a region of interest using a deep learning model for segmentation. The learning model for segmentation may identify a specific object by extracting feature values while performing pixel-wise image processing.

Two-photon fluorescence imaging is difficult to sustain for a long period of time. Therefore, it is necessary to acquire an image based on a specific time interval. For example, a brain activity image may be an image of a first interval of 1 to 3 minutes, a second interval of 7 to 9 minutes, and a third interval of 15 to 17 minutes, based on the start time of the image. The specific time interval for analysis may vary depending on the type of disease, type of pain, type of animal, type of brain area from which an image is acquired, and the like.

Figure 4:
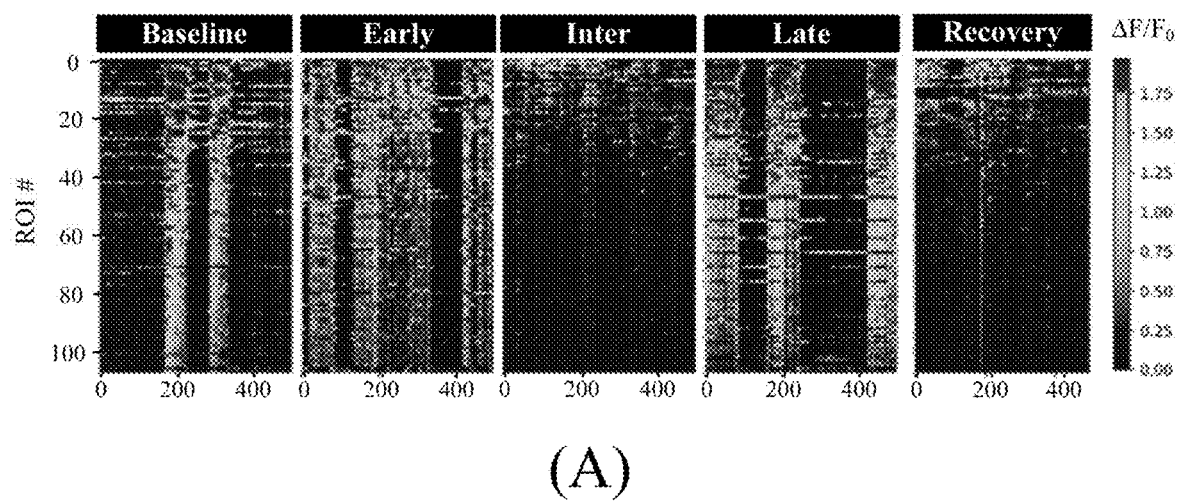
FIG. 4 is an example of an in vivo calcium imaging result.
Figure 4:
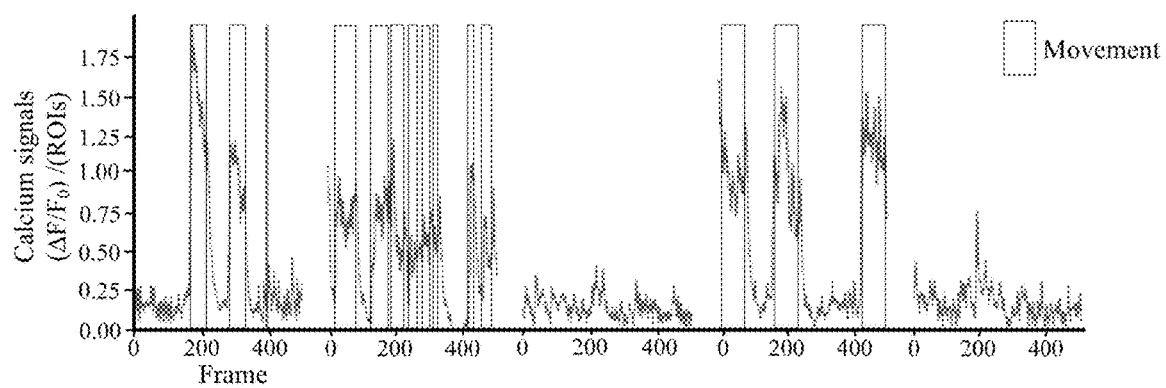

FIG. 4 is an example of an in vivo calcium imaging result. FIG. 4A is an example of a heat map expressing the rate of change in fluorescence brightness over time based on about 100 ROIs in brain activity images. In FIG. 4A, the vertical axis represents the index of the ROI, and the horizontal axis represents time. FIG. 4A shows the degree of brain activity for an ROI in five intervals (baseline, early, inter, late, recovery) with a certain length. The interval "recovery" represents a pain recovery interval. FIG. 4A shows fluorescence brightness change rates for a plurality of intervals according to time intervals.

FIG. 4B is an example of visualizing the fluorescence brightness change rates of all ROIs of a representative sample as a line graph from the average. An interval displayed as a square box in FIG. 4B represents a time interval in which a mouse is moving.

In the non-pain state, S1 neurons also have reactivity to normal movements. Accordingly, it is not easy to distinguish a pain state simply by the degree of S1 neuron activity. Accordingly, the deep learning model is utilized to distinguish the patterns of pain and non-pain in the S1 neural activity.

Figure 5:
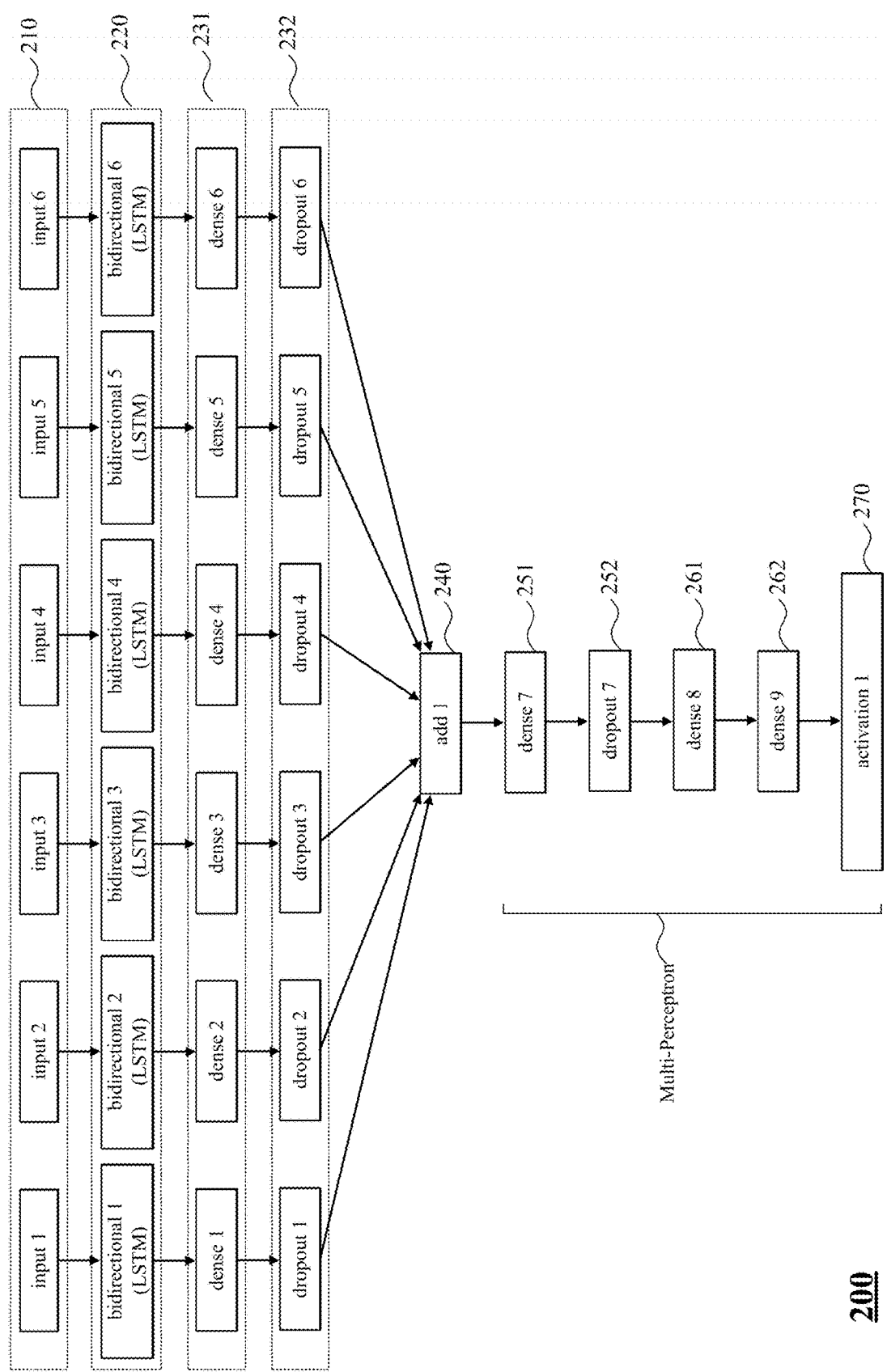
FIG. 5 is an example of a neural network model for pain assessment.

FIG. 5 is an example of a neural network model 200 for pain assessment. As described above, the brain activity image is time-series data obtained through continuous photographing in a specific interval. A typical neural network model for processing time-series data is RNN. A detailed description of the layers constituting the RNN will be omitted.

The input data may be an image of a region of interest in the brain activity image. In this case, it may be necessary to extract an ROI from an initial input image. A separate detection model (a CNN model, etc.) may extract a region of interest from the initial input image. In this case, the detection model and an RNN model configured to receive an output value of the detection model may be included.

The RNN receives an input (x), creates an output (y) through an activation function at a node of a hidden layer, and receives this output again as an input. At time t, all the neurons receive an input vector xt and an output vector yt−1 of the previous time. The RNN may have different weights for two inputs.

A long short-term memory (LSTM) is a structure in which a cell state is added to a hidden state by improving the basic RNN.

A bidirectional RNN or a bidirectional LSTM is a structure in which a hidden layer is added in the reverse direction of the time-series data. In the bidirectional LSTM, one input node is connected to a forward hidden node and a reverse hidden node, and the forward hidden node and the reverse hidden node are connected to one output node.

FIG. 5 is an example of a neural network model 200 including a bidirectional LSTM. Basically, the neural network model 200 includes an input layer stage 210, a bidirectional LSTM stage 220, a summation layer 240, a multi-perceptron layer, and an activation function layer 270.

The input layer stage 210 includes a plurality of input layers. FIG. 5 is an example having six input layers (input 1 to input 6). The plurality of input layers (input 1 to input 6) receive time-series data. The time-series data may be of the same size.

Meanwhile, the plurality of input layers (input 1 to input 6) may receive data of different lengths. The analysis device may divide the acquired time-series data into different size units, and each input layer may receive data divided into pieces of different sizes. For example, the input layer (input 1) may receive the smallest data, and the input layer (input 6) may receive the longest data.

The neural network model 200 may assess pain in units of one cell. Basically, the neural network model 200 may classify, in a binary fashion, whether a corresponding cell receives or does not receive pain at a specific time point. A specific cell may be one of a nerve cell, a glial cell, and the like.

The analysis device may output a result by inputting time-series data (an image of a region of interest) for each of a plurality of specific cells into the neural network model. The analysis device may output a result by inputting activity images of a plurality of cells (activity images in regions of interest) into the plurality of input layers (input 1 to input 6).

The bidirectional LSTM stage 220 is composed of a plurality of bidirectional LSTMs (bidirectional 1 to bidirectional 6). The plurality of bidirectional LSTMs (bidirectional 1 to bidirectional 6) are connected to the plurality of input layers (input 1 to input 6), respectively.

That is, the plurality of bidirectional LSTMs (bidirectional 1 to bidirectional 6) receive and process time-series data divided into pieces of different sizes. The plurality of bidirectional LSTMs (bidirectional 1 to bidirectional 6) output information of the same size (form). That is, for the plurality of bidirectional LSTMs (bidirectional 1 to bidirectional 6), the input data may have different sizes, and the output data may have the same size.

A dense layer stage 231 includes a plurality of dense layers (dense 1 to dense 6). The plurality of dense layers (dense 1 to dense 6) are connected to the plurality of bidirectional LSTMs (bidirectional 1 to bidirectional 6), respectively.

The dense layer has the same or similar structure as the previous connection layer. Generally, the dense layer has a structure in which input nodes and subsequent output nodes are all connected to each other. The dense layer may reduce the dimension of input data. The dense layer may output a constant value using an activation function in a hidden layer and/or an output layer.

A dropout layer stage 232 includes a plurality of dropout layers (dropout 1 to dropout 6). The plurality of dropout layers (dropout 1 to dropout 6) are connected to the plurality of dense layers (dense 1 to dense 6), respectively.

Traditionally, the dropout layer turns off neurons randomly during learning in the pre-connection layer in order to prevent over-fitting, thereby preventing learning from being biased toward training data.

The dropout layer stage 232 may have an optimal configuration.

The number of outputs of the plurality of bidirectional LSTMs (bidirectional 1 to bidirectional 6) may vary depending on the configuration. Accordingly, the dense layer stage 231 may have an optimal configuration.

The summation layer (add1) 240 may integrate output values of the previous layers. Accordingly, the summation layer 240 may integrate values output from the plurality of dense layers (dense 1 to dense 6). The summation layer 240 may integrate values output from the plurality of bidirectional LSTMs (bidirectional 1 to bidirectional 6). Furthermore, as shown in FIG. 5, the summation layer 240 may integrate values output from the plurality of dropout layers (dropout 1 to dropout 6).

The multi-perceptron layer is connected to the summation layer 240 to output a final classification value for the input data. The multi-perceptron layer refers to a hierarchical structure having an input layer, a hidden layer, and an output layer. The types and number of individual layers constituting the multi-perceptron layer may vary. The following description is based on the structure shown in FIG. 5.

A second dense layer (dense 7) 251 receives an output of the summation layer 240. A second dropout layer (dropout 7) 252 receives an output of the second dense layer (dense 7) 251.

A third dense layer (dense 8) 261 receives an output of the second dropout layer 252. A fourth dense layer (dense 9) 262 receives an output of the third dense layer (dense 8) 261. An activation function layer (activation 1) 270 receives an output of the fourth dense layer (dense 9) 262. The activation function layer (activation 1) 270 outputs a final classification value based on the input data. The activation function layer (activation 1) 270 may output a binary classification result.

Figure 6:
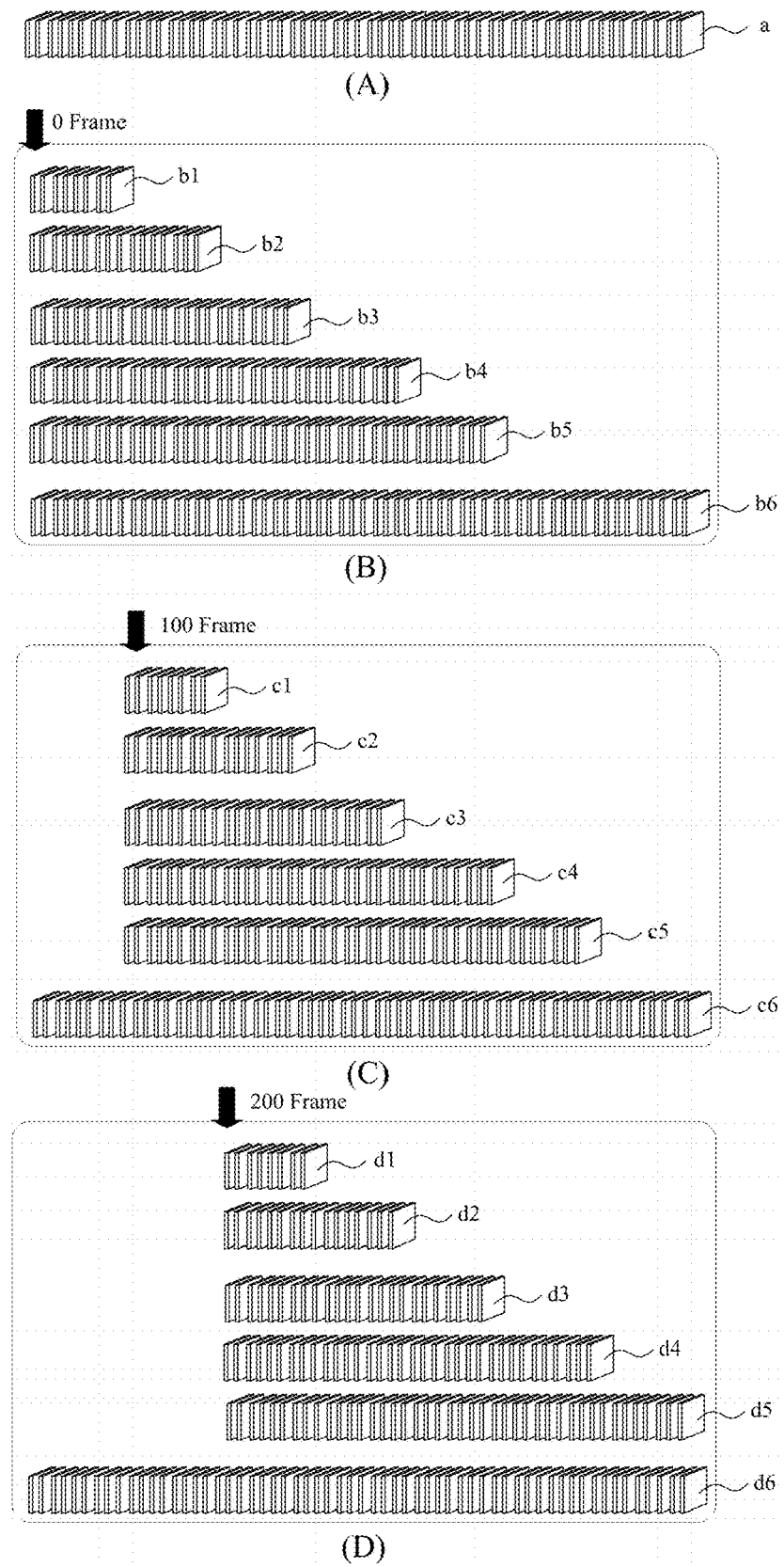
FIG. 6 is an example of a preprocessing process for data input into a neural network model.

FIG. 6 is an example of a preprocessing process for data input into a neural network model. FIG. 6 is a process of generating input data that is input into each of the plurality of input layers.

A two-photon fluorescence microscopy image corresponds to data on fluorescence brightness change rates that are continuously observed for about two minutes. In order to measure the change in pain over time while maintaining the entire time-series information, time-series data of about 2 minutes may be divided into small pieces and used as input data. The time-series data may be divided into pieces of different unit sizes.

Raw data to be divided may be data acquired in one specific time interval in FIG. 4A. For example, it is assumed that all time-series data is divided into six pieces of different sizes.

FIG. 6 illustrates a frame structure to represent image data divided into frames. FIG. 6A is an example of raw data a to be divided.

FIG. 6B is an example of dividing time-series data based on a starting point (e.g., frame 0). The same data is divided into six pieces of different sizes. The unit sizes are $b1>b2>b3>b4>b5>b6$. The size of $b6$ may be equal to the size of a. It is assumed that the size of $b1$ is 100 frames. The six divided pieces of data are input into the plurality of input layers at time t.

FIG. 6C is an example of dividing time-series data after FIG. 6B. The starting point may be continuous based on the smallest unit size. That is, the starting point may be 100 frames. The same data is divided into six pieces of different sizes. The unit size is the same as that of FIG. 6B. Thus, $c1>c2>c3>c4>c5>c6$. The six divided pieces of data are input into the plurality of input layers at time t+1.

FIG. 6D is an example of dividing time-series data after FIG. 6C. The starting point may be continuous based on the smallest unit size. That is, the starting point may be 200 frames. The same data is divided into six pieces of different sizes. The unit size is the same as that of FIGS. 6B and 6C. Thus, $d1>d2>d3>d4>d5>d6$. The six divided pieces of data are input into the plurality of input layers at time t+2.

The plurality of input layers always receives and process input data of the same size. Therefore, even when time-series data is divided into a plurality of pieces, the size of the input data is $b1=c1=d1$, $b2=c2=d2$, $b3=c3=d3$, $b4=c4=d4$, $b5=c5=d5$, and $b6=c6=d6$. FIG. 6 illustrates one example of dividing time-series data, and the division unit size, the time point at which division starts at time t+1 immediately after time t, etc. may vary.

Figure 7:
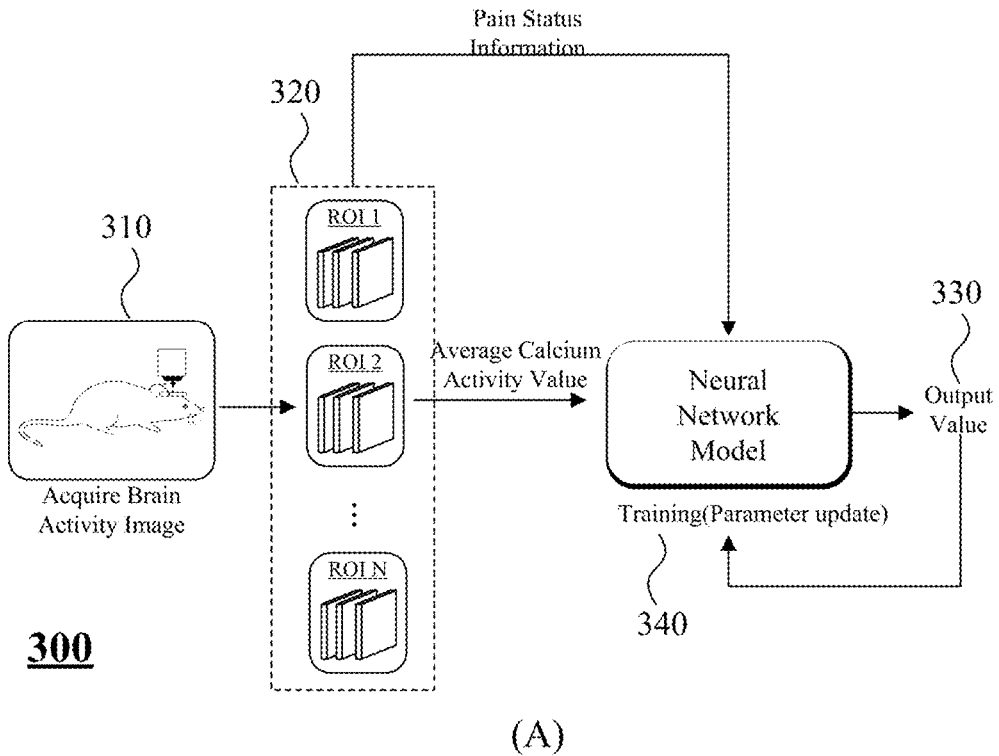
FIG. 7 is an example of a training process for a deep learning model.
Figure 7:
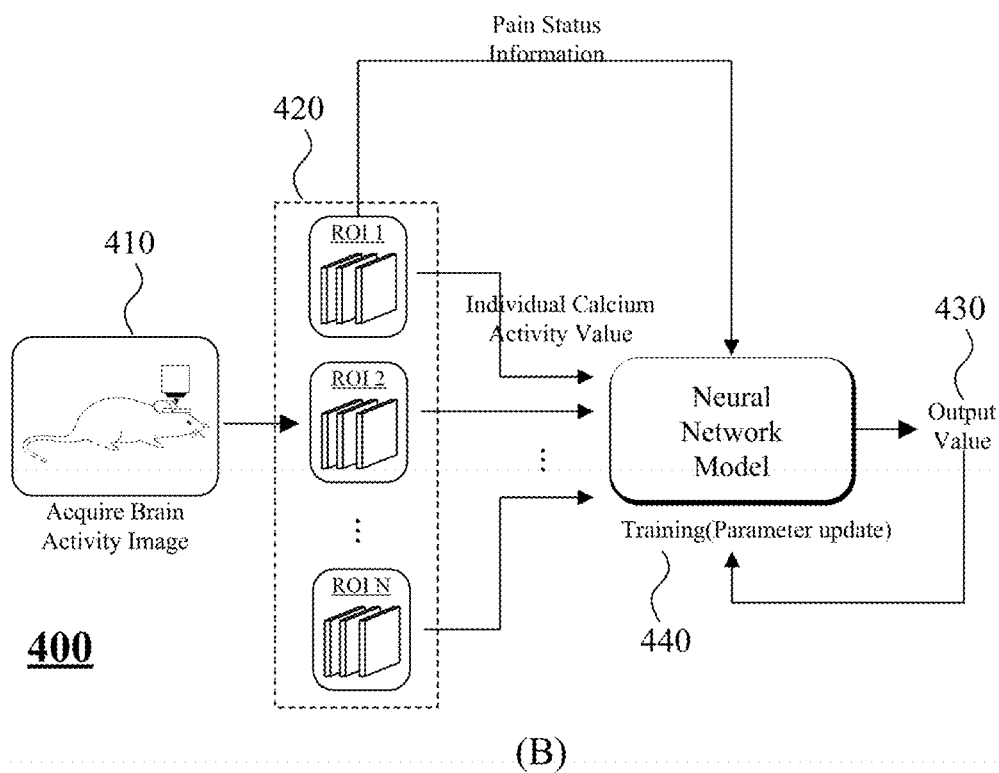

FIG. 7 is an example of a training process for a deep learning model. The training process may be performed by a separate computer device or an analysis device. It is assumed that the computer device performs the training process.

FIG. 7A is an example of a process 300 of training based on an average calcium activity value for a plurality of cells (ROIs) in a brain activity image. The computer device receives a brain activity image of a subject animal (310). In this case, the brain activity image includes images of a plurality of nerve cells. The images of the plurality of nerve cells correspond to regions of interest (ROIs). The ROIs may be set manually by developers or automatically using a separate training model or program.

The computer device averages calcium activity values for the images (ROIs) of the plurality of nerve cells (320). For example, the computer device may average fluorescence brightness change rates (delta F) representing calcium activity for the images of the plurality of ROIs. The computer device may generate a new image configured using the fluorescence brightness change rates (delta F) average for each pixel in the plurality of images. The configured new image may correspond to the average calcium activity value. The computer device inputs the average calcium activity value into a neural network model and obtains a constant output value from the neural network model (330). In this case, the computer device may input the average calcium activity value into each of a plurality of input layers, as shown in FIG. 5. The computer device compares the output value to pain state information at the time of acquiring the brain activity image and updates the parameters of the neural network model so that the output value is the same as or similar to the pain state information (340). The pain state information may be information such as a pain state or a normal state (binary classification). Alternatively, the pain state information may be one of a plurality of values indicating the degree of the pain state (multi-classification). As shown in FIG. 7A, a neural network model constructed using the average activity value of a plurality of cells (ROIs) of a sample is referred to as an average-based neural network model.

FIG. 7B is an example of a process 400 of training based on an individual calcium activity value for each of a plurality of cells (ROIs) in a brain activity image. The computer device receives a brain activity image of a subject animal (410). In this case, the brain activity image includes images of a plurality of nerve cells. The images of the plurality of nerve cells correspond to regions of interest (ROIs). The ROIs may be set manually by developers or automatically using a separate training model or program.

The computer device inputs an individual calcium activity value for each of the images (ROIs) of the plurality of nerve cells into the neural network model (420). The individual calcium activity value corresponds to a calcium image indicating the activity of one nerve cell. In this case, the computer device inputs an individual calcium activity value of each nerve cell into a corresponding one of the plurality of input layers of FIG. 5. The computer device obtains a constant output value from the neural network model (430). The computer device compares the output value to pain state information at the time of acquiring the brain activity image and updates the parameters of the neural network model so that the output value is the same as or similar to the pain state information (440). The pain state information may be information such as a pain state or a normal state (binary classification). Alternatively, the pain state information may be one of a plurality of values indicating the degree of the pain state (multi-classification). As shown in FIG. 7B, a neural network model constructed using individual activity values of a plurality of cells (ROIs) of a sample is referred to as an individual value-based neural network model.

A neural network model is constructed by the same process as shown in FIG. 7A or 7B. Subsequently, the analysis device assesses the pain of the subject animal using the trained neural network model. In this case, (1) the analysis device may input the average calcium activity value of the plurality of nerve cells in the input image into the neural network model. Alternatively, (2) the analysis device may input the individual calcium activity values of the plurality of nerve cells in the input image into the neural network model. That is, input data to be assessed for pain may also be the average calcium activity value for the plurality of nerve cells or the average of the individual calcium activity values for the plurality of nerve cells.

Figure 8:
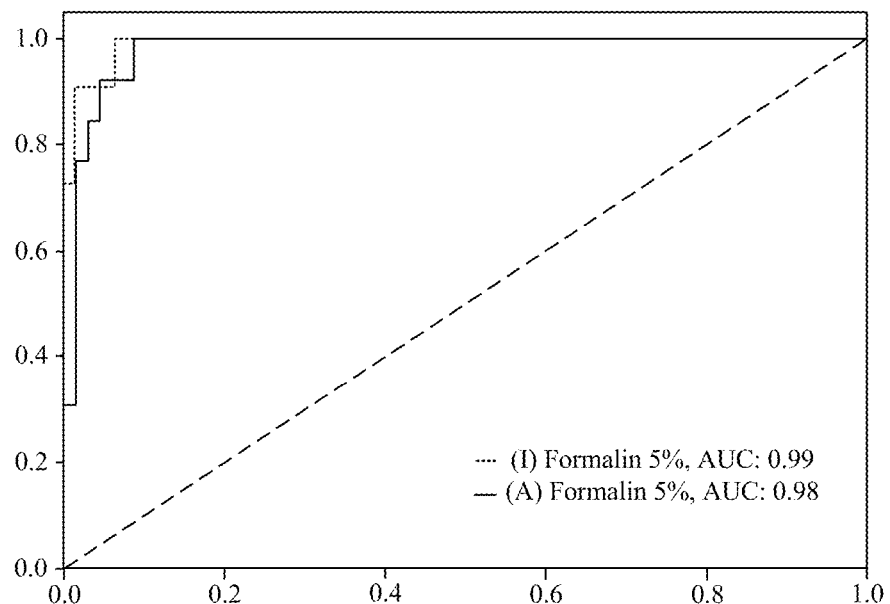
FIG. 8 is a result of evaluating the performance of an average value-based neural network model and an individual value-based neural network model.
Figure 8:
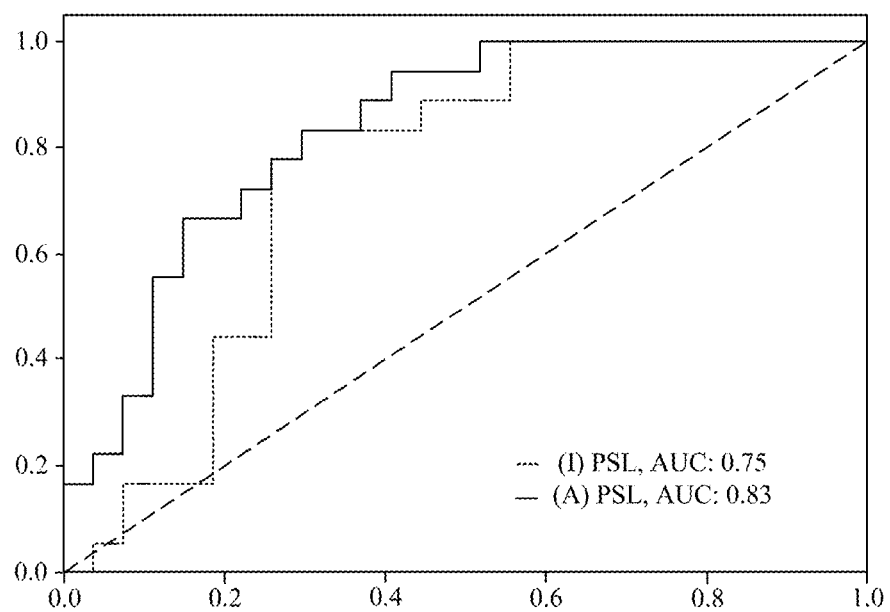

FIG. 8 is a result of evaluating the performance of an average value-based neural network model and an individual value-based neural network model. In FIG. 8, input data is an individual value of a region of interest in the performance evaluation process. That is, the input data is a result of the analysis device inputting individual values of the regions of interest into a plurality of input layers.

FIG. 8 is an evaluation of the performance of the models trained by the two methods described in FIG. 7. In the test of FIG. 8, a method of inputting images of a plurality of nerve cells into the neural network model was used.

FIG. 8A is a result of assessing formalin-induced pain. This is a result for a subject animal administered formalin 5%. In FIG. 8A, the solid line represents a result for the neural network model constructed using the average calcium activity value (Average: A), and the dotted line represents a result for the neural network model constructed using the individual calcium activity value (Individual: I). As the experimental result, for formalin-induced pain, there was little difference in performance between the model constructed using the average calcium activity value (AUC=0.98) and the model constructed using individual calcium activity values (AUC=0.99).

FIG. 8B is an analysis result for PSL pain. In FIG. 8B, the solid line represents a result for the neural network model constructed using the average calcium activity value (A), and the dotted line represents a result for the neural network model constructed using the individual calcium activity value (I). As the experimental result, for PSL pain, the model constructed using the average calcium activity value (AUC=0.83) showed higher performance than the model constructed using individual calcium activity values (AUC=0.75).

Figure 9:
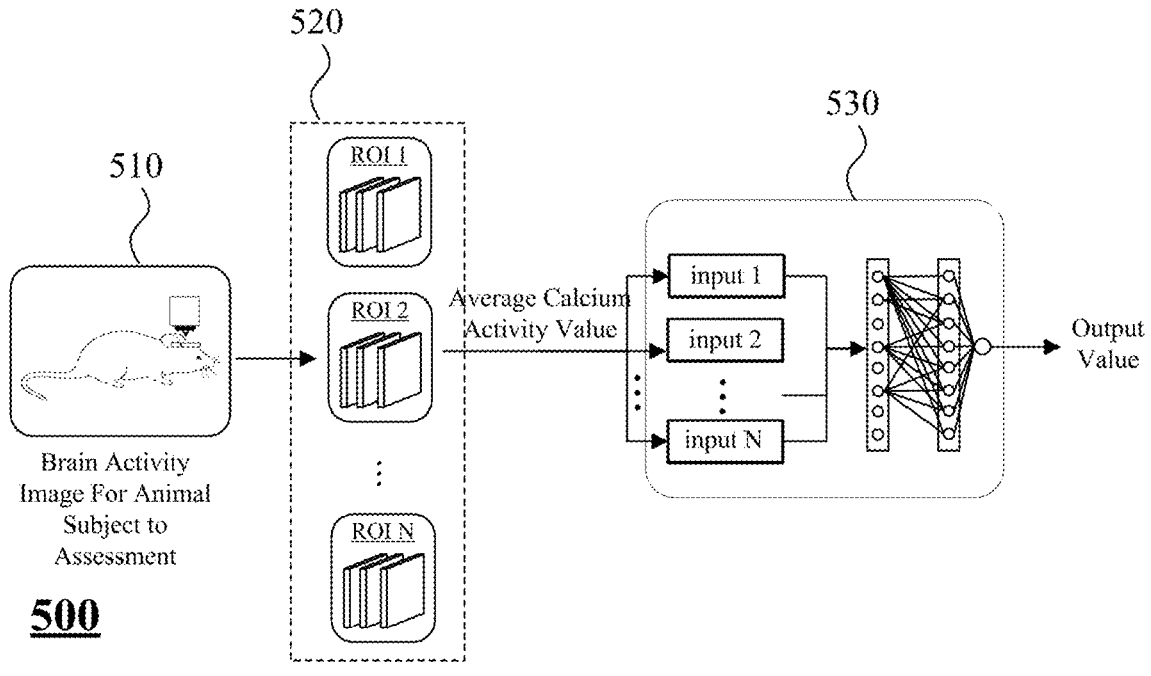
FIG. 9 is an example of a pain assessment process using an average value-based neural network model.
Figure 9:
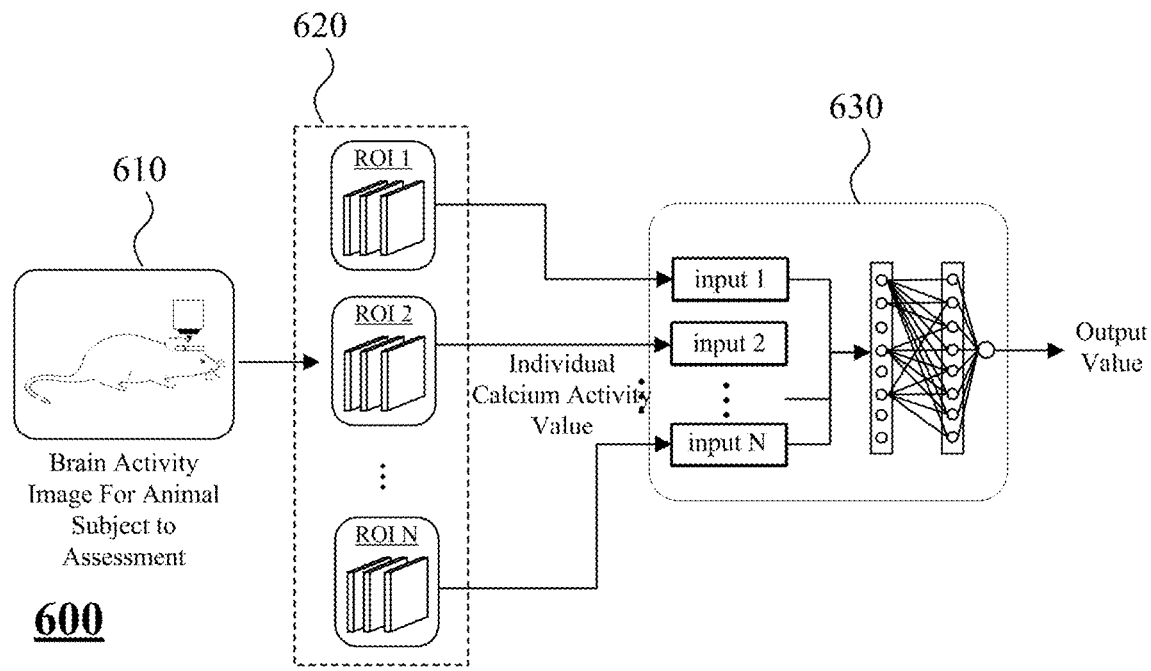

FIG. 9 is an example of a pain assessment process using an average value-based neural network model. FIG. 9 assumes that the average value-based neural network model is constructed in the manner of FIG. 7A.

FIG. 9A is an example of an assessment process 500 that uses, as input data, an average calcium activity value for a plurality of cells (ROIs) in a brain activity image. The analysis device receives a brain activity image of an animal to be assessed for pain (510). In this case, the brain activity image includes images of a plurality of nerve cells. The images of the plurality of nerve cells correspond to regions of interest (ROIs). The ROIs may be set manually by developers or automatically using a separate training model or program.

The analysis device averages calcium activity values for the images (ROIs) of the plurality of nerve cells (an average calcium activity value) (520). For example, the computer device may average fluorescence brightness change rates (delta F) representing calcium activity for the images of the plurality of ROIs. The computer device may generate a new image configured using the fluorescence brightness change rates (delta F) average for each pixel in the plurality of images. The configured new image may correspond to the average calcium activity value. The computer device inputs the average calcium activity value into a neural network model and obtains a constant output value from the neural network model (530). In this case, the computer device may input the average calcium activity value into each of a plurality of input layers of the neural network.

FIG. 9B is an example of an assessment process 600 that uses, as input data, individual calcium activity values for a plurality of cells (ROIs) in a brain activity image. The analysis device receives a brain activity image of an animal subject to assessment (610). In this case, the brain activity image includes images of a plurality of nerve cells. The images of the plurality of nerve cells correspond to regions of interest (ROIs). The ROIs may be set manually by developers or automatically using a separate training model or program.

The analysis device acquires an individual calcium activity value for each of the images (ROIs) of the plurality of nerve cells (620). The individual calcium activity value corresponds to a calcium image indicating the activity of one nerve cell. In this case, the analysis device inputs an individual calcium activity value of each nerve cell into a corresponding one of the plurality of input layers of the neural network to obtain a constant output value from the neural network model (630).

By combining the training process and the analysis process, the analysis can be performed using various methods such as one of (i) a method of performing an analysis by inputting an average calcium activity value of a sample to be analyzed into a neural network model constructed using average calcium activity values; (ii) a method of performing an analysis by inputting an individual average calcium activity value of a sample to be analyzed into a neural network model constructed using average calcium activity values, (iii) a method of performing an analysis by inputting an average calcium activity value of a sample to be analyzed into a neural network model constructed using individual calcium activity values, or (iv) a method of performing an analysis by inputting individual average calcium activity value of a sample to be analyzed into a neural network model constructed using individual calcium activity values.

The following experimental results are assessment results obtained by inputting an activity value of an individual cell into a neural network constructed using average calcium activity values.

Figure 10:
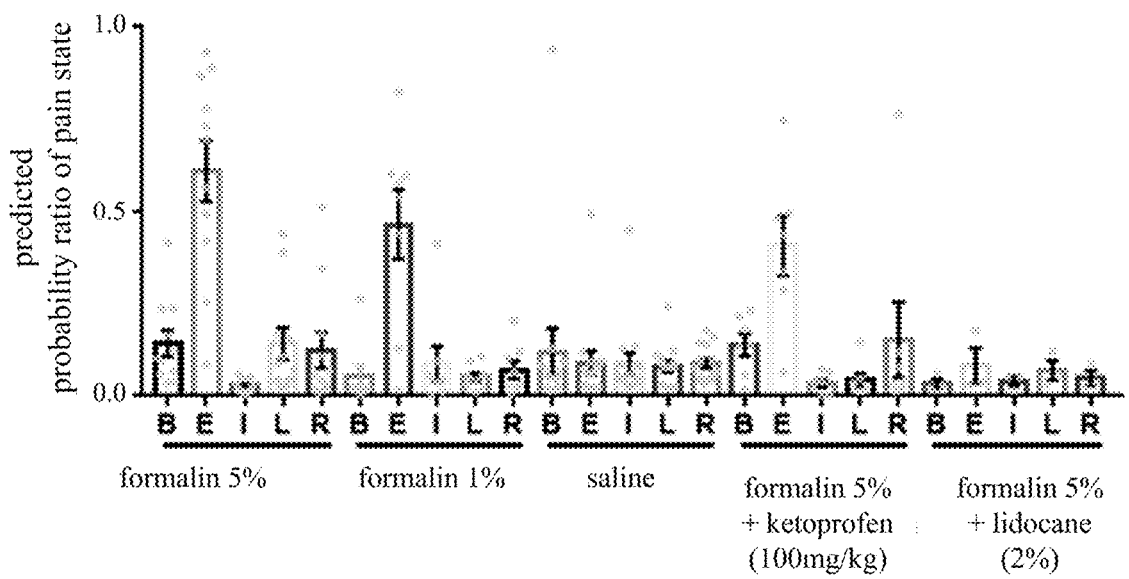
FIG. 10 is an analysis result for formalin-induced pain.
Figure 10:
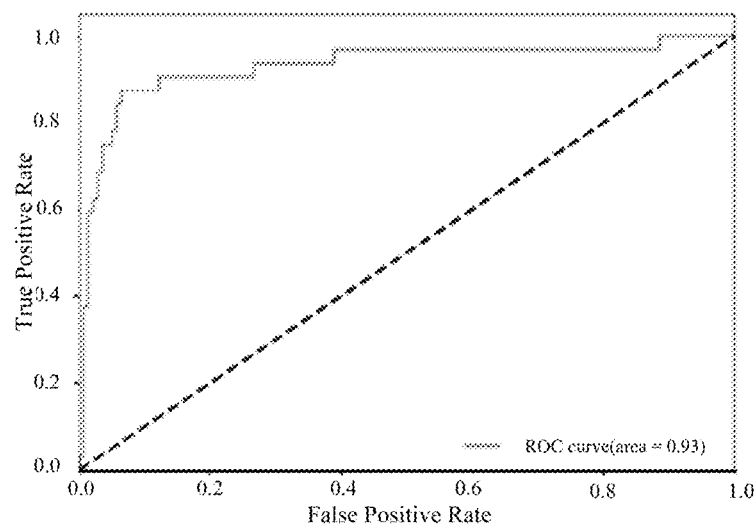
Figure 11:
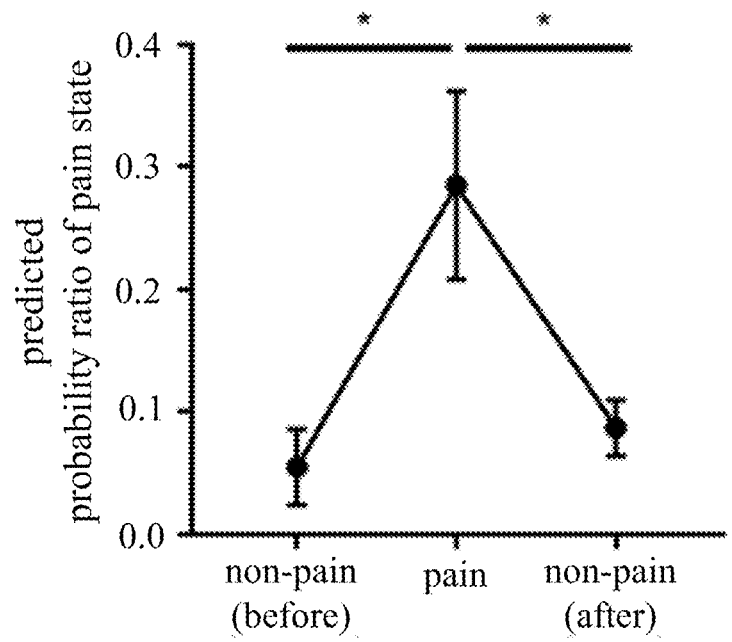
FIG. 11 is an analysis result for capsaicin-induced pain.
Figure 11:
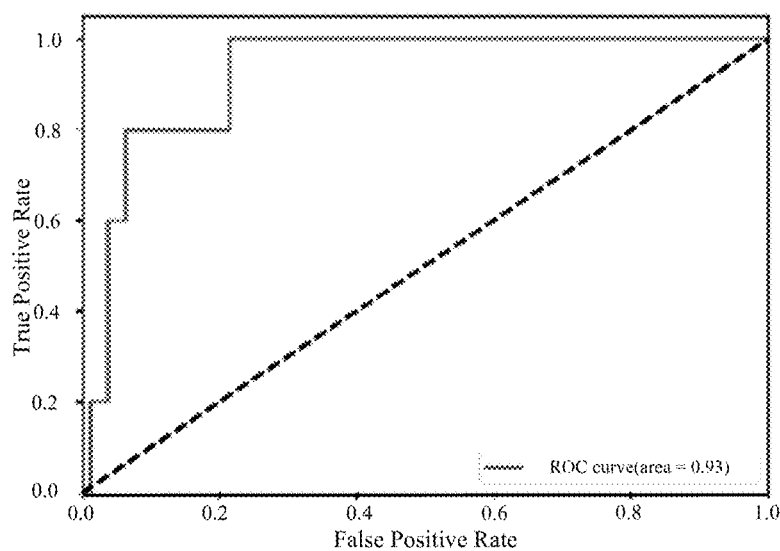
Figure 12:
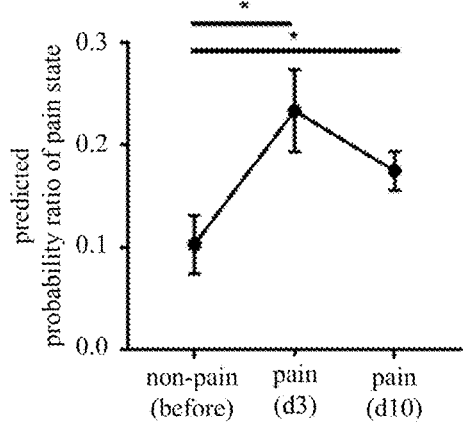
FIG. 12 is an analysis result for PSL-induced pain.
Figure 12:
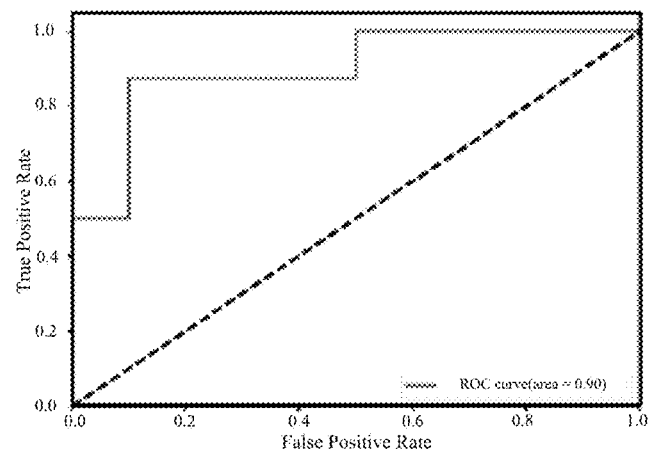
Figure 12:
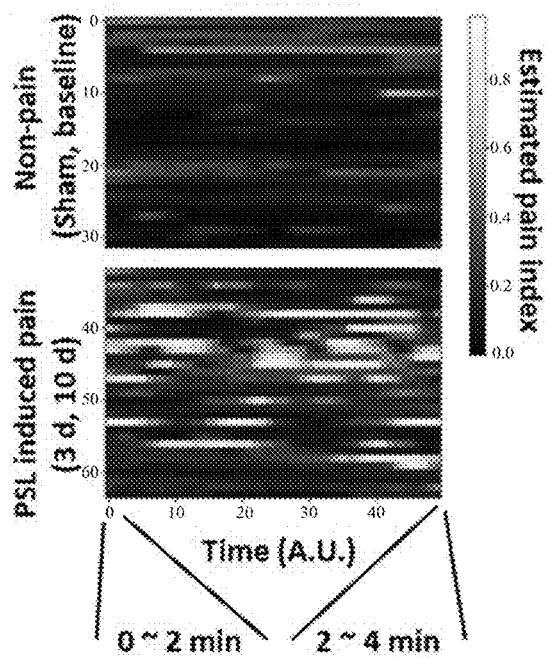

FIGS. 10 to 12 are examples of a pain assessment process using the above-described neural network model. FIGS. 10 to 12 are results obtained by assessing pain using images of cortical nerve cells.

FIG. 10 is an analysis result for formalin-induced pain.

FIG. 10A shows pain probabilities predicted when a high concentration (5%) of formalin, a medium concentration (1%) of formalin, non-painful saline, ketoprofen in addition to a high concentration of formalin, and lidocaine in addition to a high concentration of formalin are administered. FIG. 10 is divided into baseline (B), early (E), inter (I), late (L), and recovery (R) sections according to time.

Formalin pain appears only in E (early phase) as designed, and the predicted pain probability decreases with decreasing concentration and also decreases with analgesic administration. In the saline and lidocaine groups, which were predicted to be pain-free, little pain was also predicted as expected. Therefore, it can be seen that the deep learning model accurately predicts the presence and the degree of formalin-induced pain.

FIG. 10B is an ROC curve showing pain classification performance for FIG. 10A. It can be seen from the ROC curve that the AUC value is 0.93, which is a reliable level.

FIG. 11 is an analysis result for capsaicin-induced pain. FIG. 11 is a result of applying a deep learning model trained with formalin pain data to other pain causes. FIG. 11A shows a result of a higher predicted pain probability in a capsaicin pain state compared to before the administration of capsaicin and after the pain induced by the administration has sufficiently subsided. Accordingly, it can be seen that the deep learning model trained with formalin pain data can also classify pain caused by capsaicin, which is another cause of pain. FIG. 11B is an ROC curve showing pain classification performance for FIG. 11A. It can be seen from the ROC curve that the AUC value is 0.93, which is a reliable level.

FIG. 12 is an analysis result for PSL-induced pain. FIG. 12 is a result of applying a deep learning model trained with formalin pain data to other pain causes. FIG. 12A shows that the pain probability is predicted to be higher at 3 days (d3) or 10 days (d10) after the nerve damage than before the nerve damage. Accordingly, it can be seen that the deep learning model trained with formalin pain data can also predict pain appearing in the nerve damage model. FIG. 12B is an ROC curve showing pain classification performance for FIG. 12A. It can be seen from the ROC curve that the AUC value is 0.90, which is a reliable level.

A deep learning model outputs results for input data in a certain time interval. Accordingly, a user can analyze pain according to the passage of time. For example, the user may assess pain for each time period through sliding window analysis. FIG. 12C is an example of analysis results for PSL-induced pain using a sliding window. FIG. 12C shows pain states for each time window before PSL pain is induced (non-pain) and after PSL pain is induced (PSL induced pain). FIG. 12C shows that the state of pain is high after PSL is induced and that the level of pain is indicated by time period.

Table 1 below summarizes experimental result data according to FIGS. 10 to 12.

TABLE 1

|  | specificity | sensitivity | accuracy | AUC |
|---|---|---|---|---|
| formalin | 0.935 | 0.878 | 0.724 | 0.931 |
| capsaicin | 0.785 | 1 | 0.798 | 0.927 |
| PSL | 0.9 | 0.875 | 0.889 | 0.9 |

The researcher analyzed pain assessments based on areas of a brain other than cortical nerve cells. Pain assessment results using cerebellar Bergmann glial cells will be described below. Bergmann glial cells are a type of glial cell as described above. In this case, the deep learning model must be trained in advance with an image showing the activity of Bergmann glial cells of the cerebellum (e.g., a two-photon microscope image of a cerebellar region). The training data may be a two-photon microscope image of a cerebellar region and pain information (normal state or pain state) at the time of generating a corresponding image. The experimental results below are the results of the analysis device inputting individual cell activity values into the average value-based neural network model.

Figure 13:
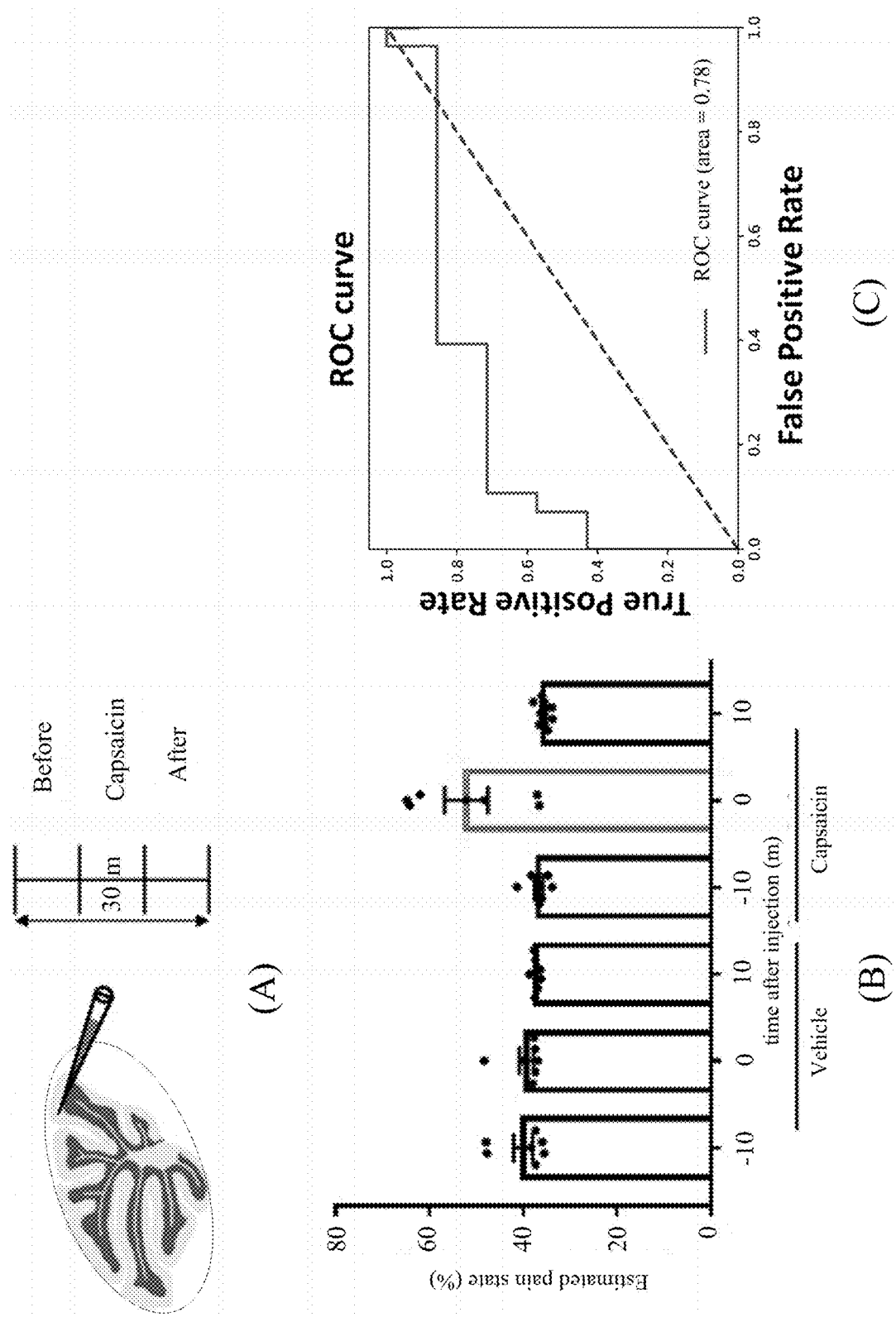
FIG. 13 is a result of assessing pain using the activity of cerebellar Bergmann glial cells.

FIG. 13 is a result of assessing pain using the activity of cerebellar Bergmann glial cells. FIG. 13A shows a cerebellar region and a capsaicin administration time. The assessment time for capsaicin was a total of 30 minutes, and the activity was assessed for 10 minutes at the time of administration and was further assessed for 10 minutes before and after administration. FIG. 13B shows a result of distinguishing a pain state based on an image of the activity of Bergmann glial cells in the cerebellar region. The reference state (Vehicle) is a state in which capsaicin is not injected. Referring to FIG. 13B, it can be seen that the pain assessment result is distinguished as a pain state for about 10 minutes after capsaicin injection. It can be seen that the pain assessment result is distinguished again as the normal state 10 minutes after capsaicin injection. FIG. 13C is an ROC curve for pain assessment using the activity of cerebellar Bergmann glial cells. The AUC is 0.78, which indicates a reliable level.

Additionally, the researcher tested whether the constructed deep learning model could distinguish itching, which is a sensory type different from pain. It will be appreciated that the deep learning model should be trained in advance using the S1 region image of the cerebral cortex and itching state information (normal state or itching state) at the corresponding time point. A model structure used for itching distinction is the same as the above-described pain distinction model.

Figure 14:
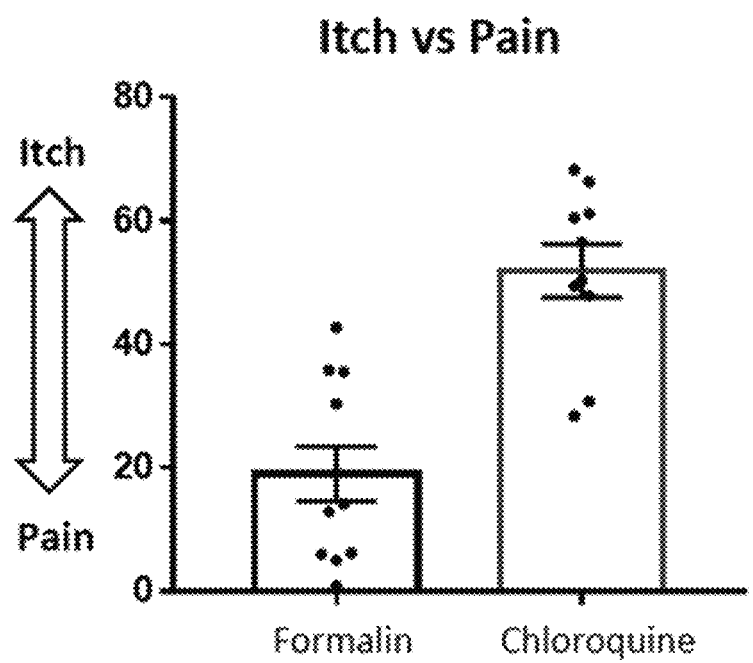
FIG. 14 is an experimental result for distinguishing pain and itching.

FIG. 14 is an experimental result for distinguishing pain and itching. The researcher induced itching by injecting chloroquine into a subject animal. FIG. 14 is a result of distinguishing the pain state (formalin) and the itching state (chloroquine). Referring to FIG. 14, it can be seen that the deep learning model almost certainly distinguishes pain and itching.

Figure 15:
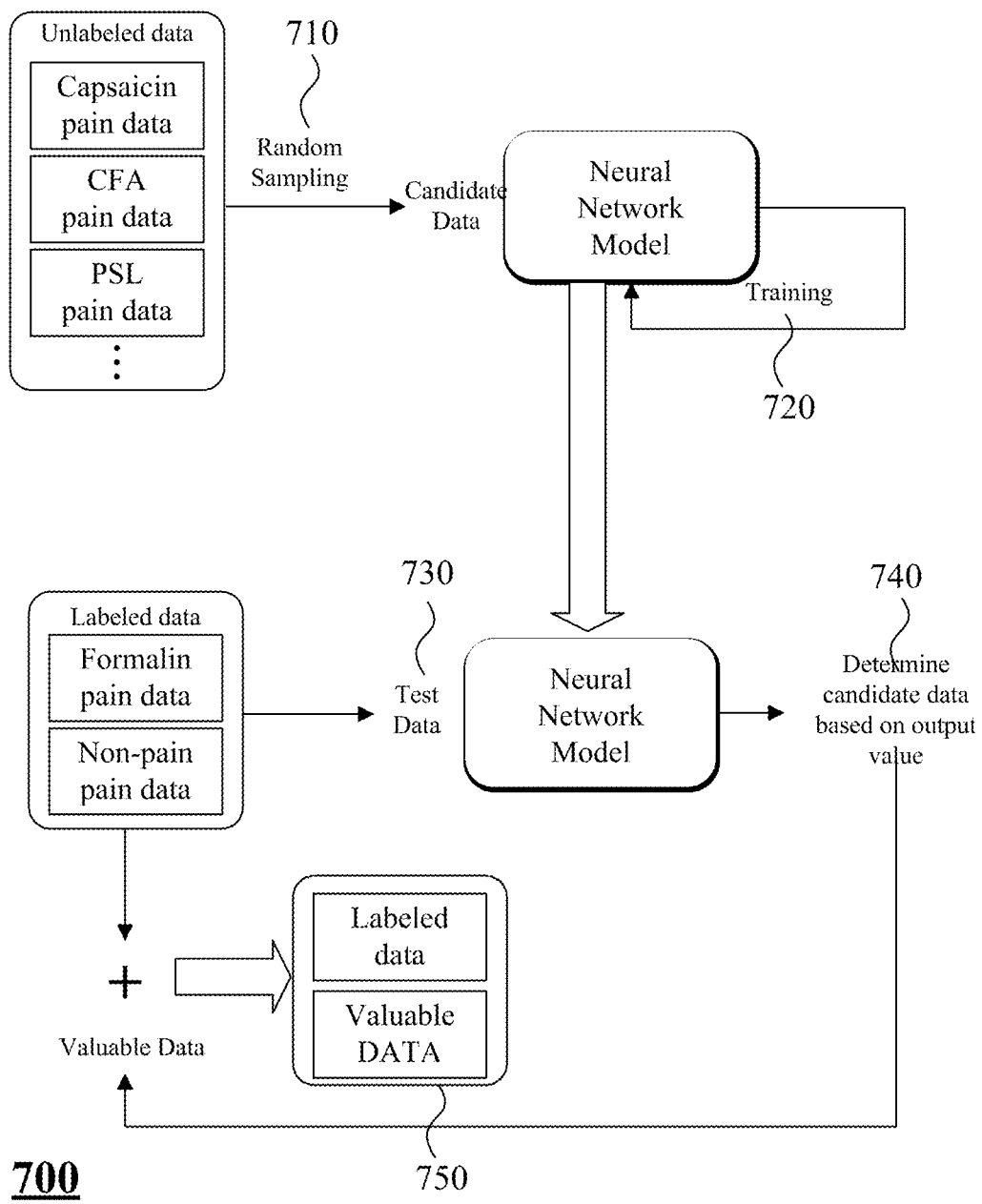
FIG. 15 is another example of a training process for a deep learning model.

FIG. 15 is another example of a training process 700 for a deep learning model. FIG. 15 corresponds to an example of a process of providing training data. FIG. 15 is an example of using a semi-supervised learning technique. The training process may be performed by a separate computer device or an analysis device. It is assumed that the computer device performs the training process.

The computer device randomly selects specific data from unlabeled data (random sampling 710) and inputs the selected data into the neural network model. The unlabeled data may include at least one type of data among various types of pain data, such as capsaicin pain data, CFA pain data, and PSL pain data.

In this process, the data selected by the computer device is called candidate data. The computer device inputs the candidate data into the neural network model to obtain a constant output value. Through this process, the neural network model is trained based on the candidate data (720).

The computer device verifies the neural network model trained in process 720 by using the labeled data. The computer device inputs specific test data of the labeled data into the neural network model (730). The computer device distinguishes the candidate data on the basis of an output value that is output from the neural network model (740). That is, when the output value that is output from the neural network model is correct, the computer device distinguishes, as valuable data, the candidate data selected in the random sampling process. Meanwhile, when the output value that is output from the neural network model is incorrect, the computer device distinguishes, as useless data, the candidate data selected in the random sampling process.

While repeating this process, the computer device identifies the valuable data among the unlabeled data. Finally, the computer device provides final training data by merging the labeled data and the valuable data (750). The computer device trains the neural network model using the final training data.

Meanwhile, the training process may use the process that has been described with reference to FIG. 7 and the like. That is, (i) time-series data having different lengths may be input into the neural network model through a plurality of input layers. (ii) The neural network model may receive an average calcium activity value of a plurality of regions of interest through the plurality of input layers. (iii) Alternatively, the neural network model may receive individual calcium activity values of the plurality of regions of interest through the plurality of input layers.

Figure 16:
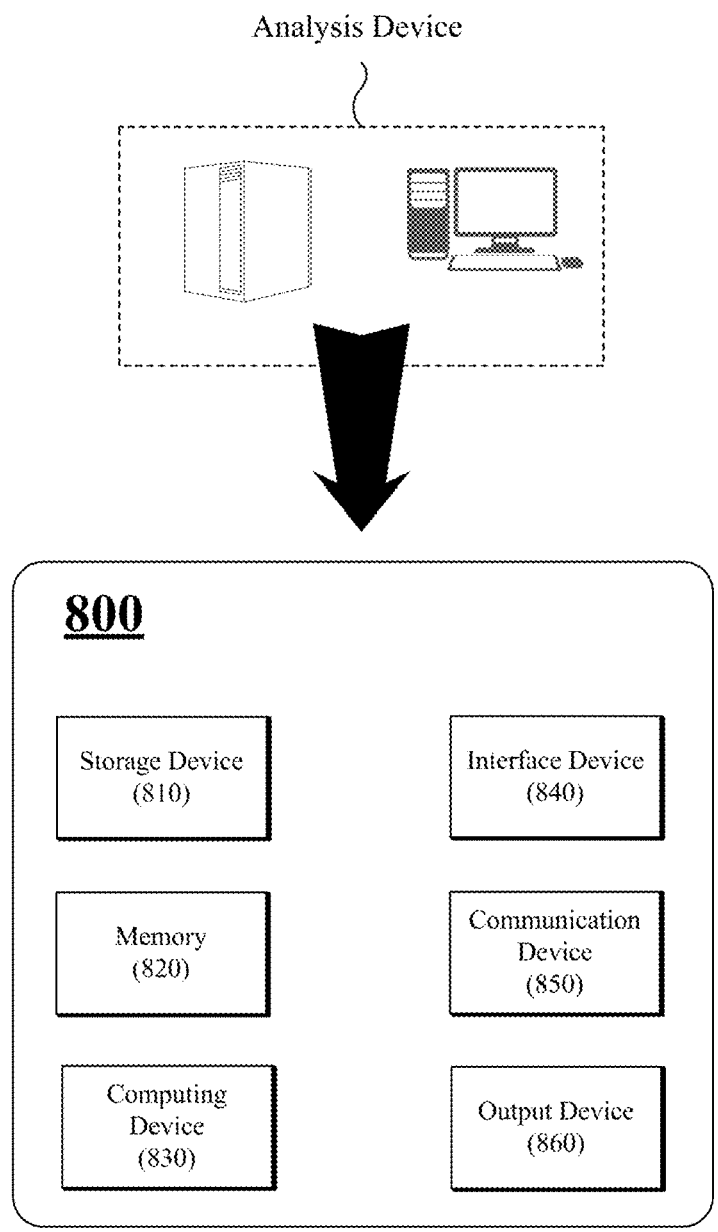
FIG. 16 is an example configuration of an analysis device for analyzing pain.

FIG. 16 is an example configuration of an analysis device for analyzing pain. An analysis device 800 is a device corresponding to the analysis device 50 or 80 of FIG. 1. The analysis device 800 analyzes and assesses the pain of an animal model using the above-described learning model. The analysis device 800 may be physically implemented in various forms. For example, the analysis device 800 may have the form of a computer device such as a PC, a server on a network, a chipset dedicated to data processing, and the like. The computer device may include a mobile device such as a smart device.

The analysis device 800 includes a storage device 810, a memory 820, a computing device 830, an interface device 840, a communication device 850, and an output device 860.

The storage device 810 stores a neural network model for assessing a pain state. The neural network model should be trained in advance. The stored neural network model may be at least one of the above-described average value-based neural network model and individual value-based neural network model.

Meanwhile, the storage device 810 may also store a neural network model capable of assessing another sensation (e.g., itching) distinct from pain.

The storage device 810 may store data and programs for training the neural network model.

The storage device 810 may store a neural network model or program for detecting a region of interest in a brain activity image.

The storage device 810 may store a program for preprocessing constant time-series data. For example, the storage device 810 may store a program for dividing the time-series data of a certain interval into a plurality of pieces of data having different sizes. Furthermore, the storage device 810 may store other programs or source code required for data processing. The storage device 810 may store the input time-series data and the analysis result.

The memory 820 may store data, information, and the like generated while the analysis device 800 analyzes received data.

The interface device 840 is a device for receiving certain commands and data from the outside. The interface device 840 may receive the brain activity image or time-series data from an external storage device or a physically connected input device. The interface device 840 may receive a learning model for data analysis. The interface device 840 may receive parameter values, information, and training data for training the learning model.

The communication device 850 refers to a component for receiving and transmitting certain information over a wired or wireless network. The communication device 850 may receive the brain activity image or the time-series data from an external object. The communication device 850 may also receive data for model training. The communication device 850 may transmit the analysis result for the input data to the external object.

The communication device 850 or the interface device 840 is a device for receiving certain commands or data from the outside. The communication device 850 or the interface device 840 may be referred to as an input device.

The input device may receive the brain activity image or the time-series data to be analyzed. For example, the input device may receive the brain activity image or the time-series data from an image generating apparatus, an external server, or a database (DB).

The brain activity image may be any one of images such as an activity image of nerve cells in the cerebral cortex and an activity image of Bergmann glial cells in the cerebellum.

Depending on the type of used input image, a deep learning model should be provided in advance. If the types of input images are diverse, a plurality of deep learning models suitable for corresponding images should be trained in advance.

Meanwhile, the time-series data may not be an image. The time-series data may be data that expresses a fluorescence value shown in a two-photon microscope image as a constant quantitative value (such as a number). In this case, the analysis device (computing device) may perform one-hot encoding for the input of the neural network model to perform pre-processing for changing into vector data.

The output device 860 is a device for outputting certain information. The output device 860 may output an interface, an analysis result, etc., that is necessary for a data processing process.

The computing device 830 may detect ROIs in an input brain activity image. Also, the computing device 830 may divide the time-series data into data units of different sizes using the program stored in the storage device 810. That is, the computing device 830 may generate input data that the learning model may receive.

The computing device 830 may input the generated input data into the learning model and assess the pain of the subject animal. The computing device 830 may input the average activity value of a plurality of cells in the input data into each input layer of the neural network. Also, the computing device 830 may input individual cell activity values in the input data into the input layers of the neural network. In this case, the computing device 830 may input the input data divided into data units of different sizes into the individual input layers.

The computing device 830 may determine whether an animal subject to assessment has pain on the basis of a value output by the neural network model.

Meanwhile, the computing device 830 may input the generated input data into the learning model to assess another sensory state (e.g., itching) of the subject animal.

The computing device 830 may learn and provide a neural network model using one of the above-described learning methods. The computing device 830 may train the learning model used for the assessment of pain of the subject animal using given training data.

The computing device 830 may be a device, such as a processor, an application processor (AP), and a chip with an embedded program, for processing data and processing some computations.

Also, the above-described pain assessment method for target animals may be implemented using a program (or application) including an executable algorithm that may be executed by a computer. The program may be stored and provided in a transitory or non-transitory computer-readable medium.

The non-transitory computer-readable medium refers to a medium that semi-permanently stores data and is readable by a device rather than a medium that temporarily stores data such as a register, a cache, and a memory. Specifically, the above-described various applications or programs may be stored and provided in a non-transitory computer-readable medium such as a compact disc (CD), a digital versatile disc (DVD), a hard disk, a Blu-ray disc, a Universal Serial Bus (USB), a memory card, a read-only memory (ROM), a programmable read-only memory (PROM), an erasable PROM (EPROM), an electrically EPROM (EEPROM), or a flash memory.

A transitory computer-readable medium refers to various RAMs such as a static RAM (SRAM), a dynamic RAM (DRAM), a synchronous DRAM (SDRAM), a double data rate SDRAM (DDR SDRAM), an enhanced SDRAM (ESDRAM), a SyncLink DRAM (SLDRAM), and a Direct Rambus RAM (DRRAM).

According to the above technique, it is possible to assess pain based on brain activity of an experimental animal, thus enabling quantitatively accurate analysis. According to the above technique, it is possible to assess pain for chronic pain models, such as neuropathic pain models. Also, according to the above technique, it is possible to determine the occurrence of pain for each time period in detail. Therefore, the above technique can be utilized for the study of persistent pain by overcoming the limitations of conventional pain determination methods and revealing how nerve cells express pain.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method for pain assessment using a deep learning model, the method comprising:
   receiving, by an analysis device, an image indicating activity in a specific brain area of a subject animal; and
   allowing the analysis device to input images of regions of interest in the image into a neural network model and assess pain of the subject animal according to a result output by the neural network model,
   wherein each region of interest is a region indicating the activity of an individual cell, and the analysis device inputs information generated based on the images of the regions of interest into a plurality of input layers of the neural network model, and
   wherein the images are time-series data in a certain time interval, and the analysis device divides time-series data for the regions of interest into units of different sizes and inputs the time-series data divided into the units of different sizes into different input layers of the plurality of input layers.

2. The method of claim 1, wherein the analysis device is configured to:
   divide the time-series data into the units of different sizes on a basis of a first time point at which the division of the unit of the size into smallest units is started in the certain time interval and input a plurality of pieces of time-series data divided at the first time point among the time-series data into the plurality of input layers; and
   divide the time-series data into the units of different sizes on a basis of a second time point at which the division into the smallest units is started after the first time point and input a plurality of pieces of time-series data divided at the second time point among the time-series data into the plurality of input layers.

3. The method of claim 1, wherein the image is a multi-photon microscope image indicating brain activity.

4. The method of claim 1, wherein the image is a fluorescence image indicating an activity state for a primary somatosensory area (S1) of a cerebral cortex.

5. The method of claim 1, wherein the image is an image indicating an activity state for a Bergmann glial cell in a cerebellum.

6. The method of claim 1, wherein the neural network model is a bidirectional recurrent neural network model.

7. The method of claim 1, further comprising operations of:
   receiving, by a plurality of input layers, the images of the regions of interest while the neural network model performs the following operations to assess the pain;
   receiving, by a plurality of bidirectional long short-term memories (LSTMs), outputs of the plurality of input layers;
   allowing outputs of the plurality of bidirectional LSTMs to be integrated;
   receiving, by a dense layer, the integrated value; and
   receiving, by an activation function layer, an output of the dense layer.

8. The method of claim 1, wherein the neural network model is trained by equally inputting an average value of information indicating the activity of a plurality of nerve cells in a brain activity image into the plurality of input layers.

9. A device for pain analysis using a deep learning model, the pain analysis device comprising:
   an input device configured to receive an image indicating activity in a specific brain area of a subject animal;
   a storage device configured to store a bidirectional recurrent neural network model that receives an image for brain activity and assesses a pain state; and
   a computing device configured to input images of regions of interest in the image into a plurality of input layers of the bidirectional recurrent neural network model and assess pain of the subject animal according to a result output by the bidirectional recurrent neural network model,
   wherein each region of interest is a region indicating the activity of an individual cell, and
   wherein the images are time-series data in a certain time interval, and the computing device divides time-series data for the regions of interest into units of different sizes and inputs the time-series data divided into the units of different sizes into different input layers of the plurality of input layers.

10. The device of claim 9, wherein the image is a multi-photon microscope image indicating brain activity.

11. The device of claim 9, wherein the image is a fluorescence image indicating an activity state for a primary somatosensory area (S1) of a cerebral cortex or an image indicating an activity state for a Bergmann glial cell in a cerebellum.

12. The device of claim 9, wherein the computing device inputs pixel values or images of the regions of interest into the plurality of input layers or equally inputs an average value of average pixel values of the regions of interest into the plurality of input layers.

13. The device of claim 9, wherein the bidirectional recurrent neural network model is trained by equally inputting an average value of information indicating the activity of a plurality of nerve cells in a brain activity image into the plurality of input layers.

* * * * *